(12) United States Patent
Guth et al.

(10) Patent No.: US 8,667,829 B2
(45) Date of Patent: *Mar. 11, 2014

(54) BREATH TEST SIMULATOR AND METHOD

(75) Inventors: Richard U. Guth, Harrisburg, PA (US); Shawn P. Barry, Millersburg, PA (US)

(73) Assignee: Guth Laboratories, Inc., Harrisburg, PA (US)

( * ) Notice: Subject to any disclaimer, the term of this patent is extended or adjusted under 35 U.S.C. 154(b) by 493 days.

This patent is subject to a terminal disclaimer.

(21) Appl. No.: 13/009,960

(22) Filed: Jan. 20, 2011

(65) Prior Publication Data

US 2011/0107813 A1    May 12, 2011

Related U.S. Application Data

(63) Continuation of application No. 12/574,921, filed on Oct. 7, 2009, now Pat. No. 7,895,878.

(51) Int. Cl.
*G01N 21/00* (2006.01)
*G01N 31/00* (2006.01)

(52) U.S. Cl.
USPC ............................................ 73/1.03; 436/9

(58) Field of Classification Search
USPC .................. 73/1.03, 1.06, 23.3; 436/9
See application file for complete search history.

(56) References Cited

U.S. PATENT DOCUMENTS

| | | | |
|---|---|---|---|
| 6,526,802 B1 * | 3/2003 | Fisher et al. | 73/1.03 |
| 7,404,311 B2 * | 7/2008 | Guth et al. | 73/1.03 |
| 7,493,793 B2 * | 2/2009 | Guth et al. | 73/1.03 |
| 7,543,472 B2 * | 6/2009 | Crespo et al. | 73/1.06 |
| 7,895,878 B1 * | 3/2011 | Guth et al. | 73/1.03 |
| 2007/0261468 A1 * | 11/2007 | Crespo et al. | 73/1.03 |
| 2008/0060408 A1 * | 3/2008 | Guth et al. | 73/1.03 |
| 2008/0060409 A1 * | 3/2008 | Guth et al. | 73/1.03 |

* cited by examiner

*Primary Examiner* — Hezron E Williams
*Assistant Examiner* — Nathaniel Kolb
(74) *Attorney, Agent, or Firm* — Hooker & Habib, P.C.

(57) ABSTRACT

A breath test simulator for supplying a breath test analyzer with a vapor including ethyl alcohol includes a heated thermal mass to heat an inlet passage.

21 Claims, 7 Drawing Sheets

BREATH TEST SIMULATOR AND METHOD

FIELD OF THE DISCLOSURE

The disclosure relates to a breath test simulators that generates a vapor sample containing a precisely controlled concentration of ethyl alcohol and flows the vapor sample to a breath test analyzer for calibrating the analyzer.

DESCRIPTION OF THE PRIOR ART

U.S. Pat. No. 7,493,793 describes an efficient breath test simulator with a thermally conductive aluminum lid closing the top of a jar containing a water/ethyl alcohol solution having a known concentration of ethyl alcohol. The solution is heated to a regulatory allowable operating temperature range between 33.80° C. and 34.20° C. The headspace above the solution is also heated. The regulatory allowable operating temperature range for the solution is determined in the United States by the National Highway Traffic Safety Administration (NHTSA).

An unheated breath sample is flowed through a thin wall air inlet tube into the jar and bubbles up through the solution to absorb a known amount of ethyl alcohol from the solution. The resulting vapor is collected in the headspace above the solution. The inlet tube is in a cavity above the lid and can cool the breath sample so that the sample cools the solution. Vapor is flowed from the headspace through an air outlet tube to a breath test analyzer for calibrating the analyzer.

The solution is heated by a small immersion heater actuated by a temperature control circuit having a temperature sensor in the solution. The temperature control circuit maintains the solution in a normal range in the center of the regulatory allowable operating range. A display indicates the temperature of the solution as determined by the temperature sensor used by the temperature control circuit.

A resistance heater on the lid maintains the lid at a temperature slightly above the solution temperature. The heated lid heats the headspace. Heat from the heater is conducted through the lid to the air inlet and outlet tubes. The tubes are in the cavity and cool rapidly when the lid heater is off.

The outlet and inlet tubes of the simulator illustrated in U.S. Pat. No. 7,493,793 are formed by welding brass tubing which is subsequently plated to provide a protective metal coating. This manufacturing process is expensive and time consuming.

SUMMARY OF THE DISCLOSURE

The disclosure is an improved breath test simulator with a top housing mounted over the mouth of a jar containing a water/ethyl alcohol solution. The housing is preferably formed from a machined body of conductive metal and includes a lid and a passage projection on the lid. A breath test sample inlet passage and a vapor outlet passage extend through the passage projection. The projection is preferably formed from the same piece of metal forming the lid and serves as a thermal mass for warming the inlet and outlet passages. The simulator includes a heater for the lid. The heater heats the lid, the passage projection and the passages in the projection.

The passage projection is surrounded by air. The metal in the projection prevents this air, which typically is cooler than the solution, from cooling the passages.

The metal in the projection surrounding the passages prevents rapid fluctuation of the temperature in the passages despite on/off cycling of the lid heater. Maintaining the inlet passage at a stable temperature close to the temperature of the solution heats the inlet air so that when the heated inlet air is bubbled into the solution it does not cool the solution. The heated inlet air reduces the need to heat the solution.

Forming the top housing from a single piece of conductive metal reduces manufacturing cost and reduces the time required for making the housing.

The disclosed breath test simulator uses two independent control circuits. An independent temperature control circuit maintains the temperature of the solution in the jar within a normal operating range located at the approximate center of the regulatory allowable operating range. An independent temperature monitoring circuit generates a solution temperature signal which is displayed on the lid and is used to determine if the solution temperature is outside a simulator allowable operating range located inside the regulatory allowable temperature range. The simulator allowable range has upper and lower temperature limits very close to and inside the limits of the regulatory allowable operating range.

When the temperature of the solution is within the simulator allowable operating range, the temperature monitoring circuit displays the solution temperature. When the temperature of the solution is above or below the simulator allowable operating range, the temperature monitoring circuit displays alternate error messages and "Temperature High" or "Temperature Low" messages, and turns off the solution and lid heaters, turns off the agitator drive, and actuates an audible alarm indicating the solution temperature is outside the simulator allowable operating range.

The temperature control circuit and the temperature monitoring circuit are independent of each other. Each circuit includes a dedicated temperature sensor located in the solution in the jar. The two independent circuits assure that the temperature of the solution in the simulator is in the regulatory allowable operating range during calibration of a breath test analyzer. If the solution temperature approaches the limits of the regulatory allowable operating range, the simulator is shut down and alarm signals are displayed and broadcast.

DESCRIPTION OF THE PREFERRED EMBODIMENT

Figure 1:
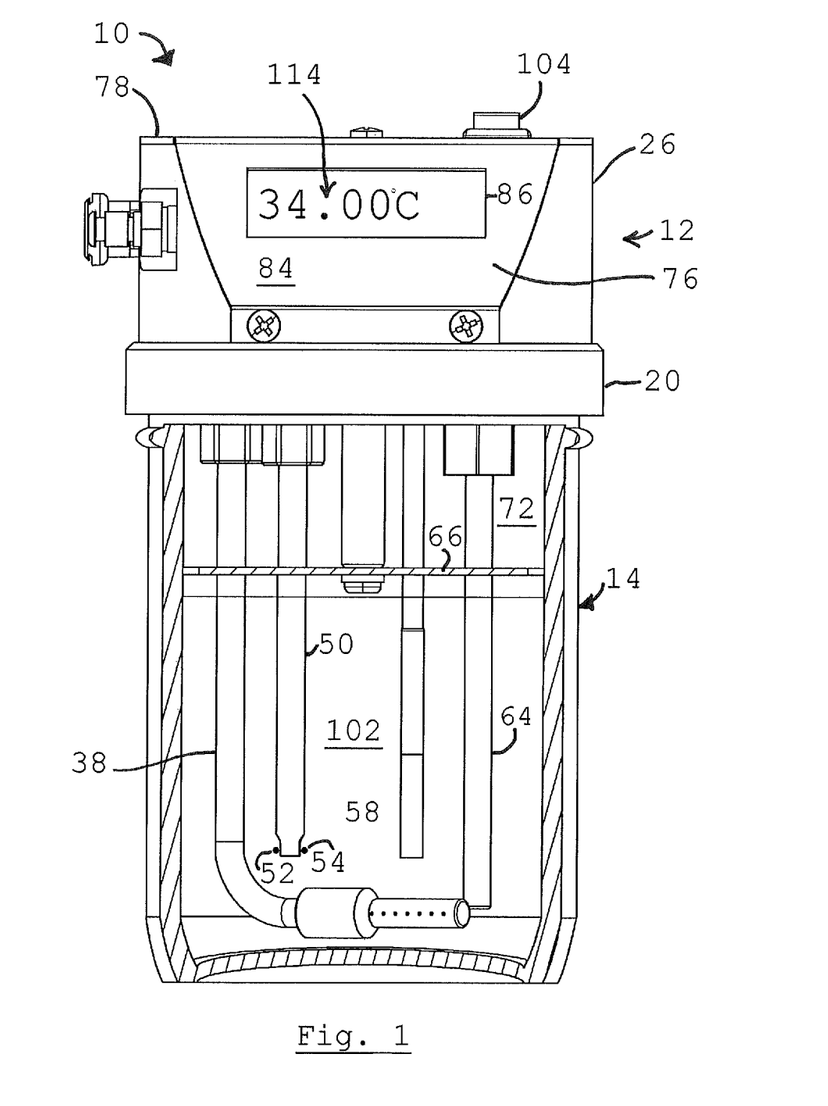
FIG. 1 is a side view of a breath test simulator, partially broken away.
Figure 2:
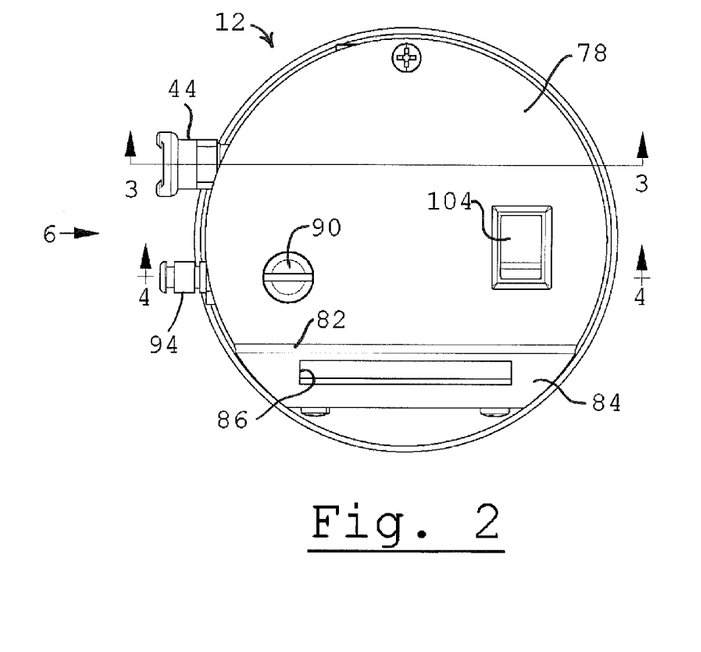
FIG. 2 is a top view of the simulator of FIG. 1.
Figure 3:
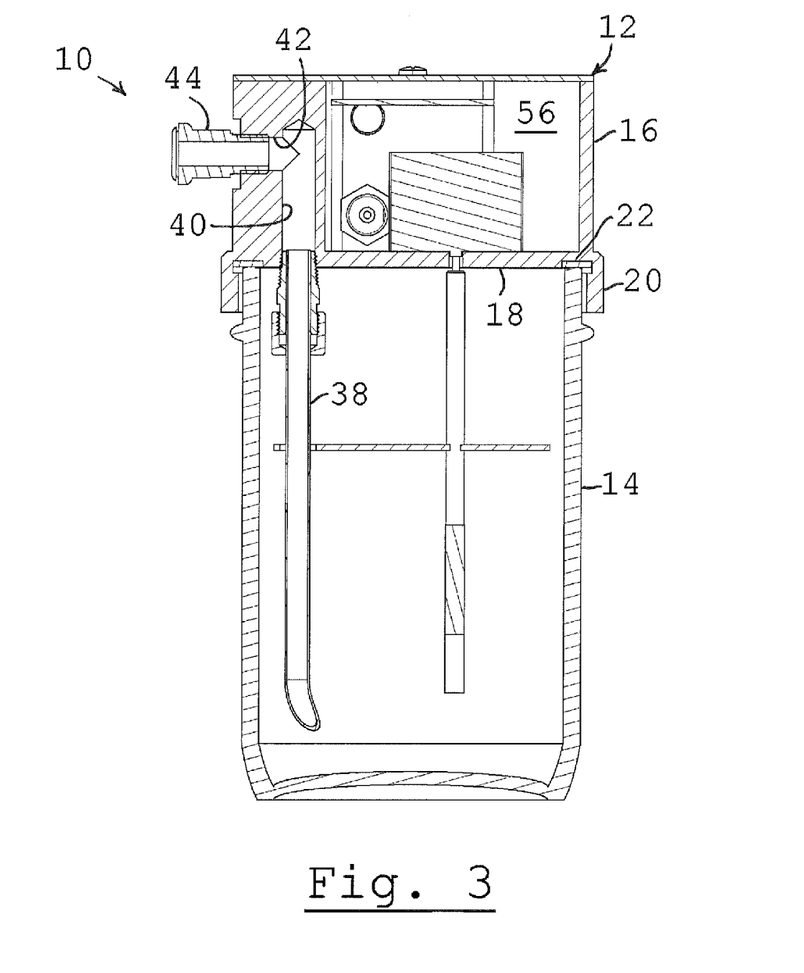
FIG. 3 is a sectional view taken along line 3--3 of FIG. 2.

Breath test simulator 10 includes top housing 12 and a plastic or glass container or jar 14 mounted on the housing. The housing includes a metal body 16 including a flat, circular lid 18 with downwardly extending circumferential lip 20. The inner surface of the lip 20 and outer surface of the top of jar 14 include complementary threads which permit threaded engagement of the housing on the top of the jar. A circular sealing gasket 22 is mounted in a recess on the edge of the bottom of lid 18 to engage the top of the jar 14 when the housing is mounted on the jar, as shown in FIG. 3.

Figure 7:
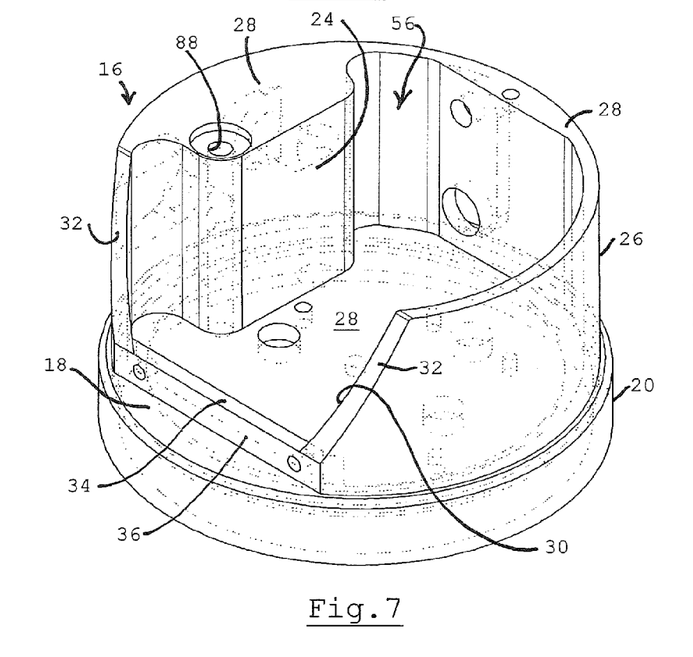
FIG. 7 is a perspective view of a top housing body used in the simulator.

Body 16 as shown in FIG. 7 and includes a passage projection 24 and circumferential wall 26 extending upwardly above the top surface 28[1] of lid 18. The circumferential wall 26 extends from one side of the projection 24 around the circumference of the lid to the other side of the projection 24. The projection 24 and wall 26 have a flat top surface 28 extending from the projection around the wall to angled wall recess 30 having opposed sides 32 angling down from the top surface 28 of wall 26 to the top surface 34 of lower wall 36. If desired, the projection may extend below the lid.

Body 16 is preferably formed from a single piece of metal having a high co-efficient of thermal conductivity, and may be made from aluminum. The single piece construction of body 16 improves heat flow throughout the body during heating of the lid and heating of the projection 24 and the passages in the projection. If desired, the body may be made of a number of metal parts where the parts are held together in tight surface-to-surface contact to promote flow of heat throughout the body. The metal in the passage projection forms a large thermal mass for heating the inlet and outlet passages extending through the projection and maintaining the temperature in the passages constant, despite cycling of the lid heater 118.

The lid 18 supports a number of components extending downwardly into the interior of jar 14. Air inlet tube 38 is mounted on the lid in flow communication with vertical inlet passage portion 40 and intersecting horizontal inlet passage portion 42. Passage portions 40 and 42 are formed in projection 24. Air inlet port 44 is connected to passage portion 42 on one side of housing 12. An air inlet line is connected to port 44 to flow air through the air inlet passage 42, 40 and to tube 38. Tube 38 has a lower end 46 at the bottom of the jar. Small air dispersion holes 48 are provided at tube end 46 for dispersing air flowed through the tube into the water/ethyl alcohol solution in the jar.

Temperature sensor rod 50 is mounted on lid 18 and extends downwardly into the solution in jar 14. Two independent temperature sensors 52 and 54 are secured to the lower end of rod 50 in the solution. The sensors may be thermistors. Electrical leads for the two sensors extend upwardly through the interior of the rod and into cavity 56 formed in body 16. The leads are connected to controllers mounted in the cavity and illustrated in FIG. 9, as described below.

Rotary stirrer rod 58 extends downwardly into the solution in jar 14 from the lid and carries agitator 60. The rod 58 extends through an opening in the lid and is mounted on the output shaft of electric stirrer motor 62 mounted on the top of the lid in cavity 56.

Figure 4:
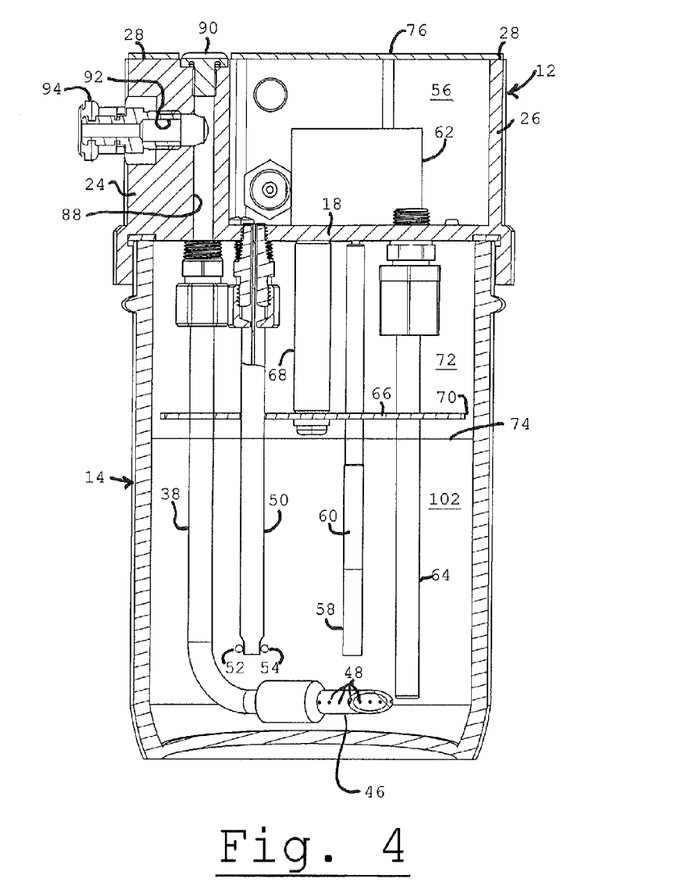
FIG. 4 is a sectional view taken along line 4--4 of FIG. 3.

Circular solution baffle plate 66 is mounted on support rod 68 extending downwardly from lid 18. Plate 66 has an outer edge spaced a short distance in from the inner wall of the jar to provide a narrow circumferential gap 70 between the plate and jar. Air bubbled up through the solution from holes 48 rises to the top of the solution and the bubbles collapse. The plate 66 prevents droplets of solution released by the collapse of the bubbles from entering the headspace 72 in the top of the jar between plate 66 and lid 18. Tube 38, and rods 50, 58 and 64 extend through plate 66 as shown in FIG. 4.

The lower portion of jar 14 is filled with an ethyl alcohol-water solution having a known concentration of ethyl alcohol. The top surface 74 of the water-ethyl alcohol solution is located a short distance below plate 66.

Heater rod 64 is mounted on lid 18 and extends downwardly into the solution in jar 14. The heater rod includes a heater, which may be an electric resistance heater, a small halogen light or other electrical heating element for heating the solution in the jar when actuated by circuitry mounted in cavity 56.

Figure 8:
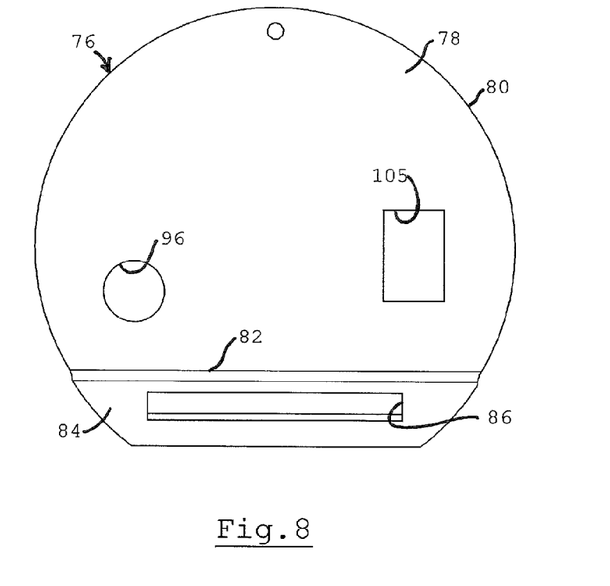
FIG. 8 is a top view of a cover mounted on top of the body of FIG. 7.

Top housing 12 includes a sheet metal cover 76 which closes the top of cavity 56. Cover 76 is illustrated in FIG. 8. The cover 76 includes a flat, partial circular top having a round outer edge 80 overlying the partial circular wall top surface 28 and extending between the ends of chord 82. A flat, angled display wall 84 extends downwardly at an angle from a bend at chord 82. Rectangular display window 86 is formed in wall 84. An electronic temperature display panel on wall 84 is viewed through window 86. The cover is mounted on the top of body 16 by use of screws to engage the body top surface 28, angled sides 32 and the outer surface of lower wall 36 as illustrated.

Master on/off switch 104 is mounted in opening 105 on top 78 of cover 76. Switch 104 actuates and de-actuates the electrical components of simulator 10.

Figure 6:
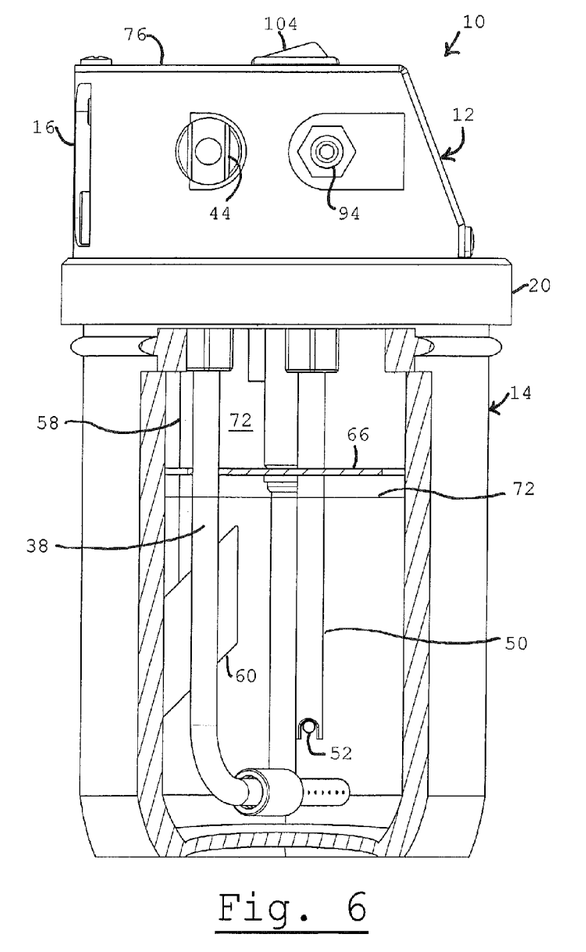
FIG. 6 is a side view of the simulator taken in the direction of arrow 6 shown in FIG. 2, partially broken away.

Body 16 includes a vapor outlet passage having a section 88 extending vertically up from the bottom of the lid through projection 24 to the top of the projection. Threaded plug 90 removeably closes a port at the top of passage section 88. Horizontal outlet passage section 92 in projection 24 is located below plug 90 and extends from passage section 88 to the circumferential side of housing 12. Vapor outlet port 94 is mounted on the end of passage section 92 to permit connection of a tube to flow headspace vapor discharged from the simulator to a breath test analyzer to be calibrated by the simulator. Outlet port 94 is adjacent inlet port 44 as illustrated in FIG. 6.

Figure 5:
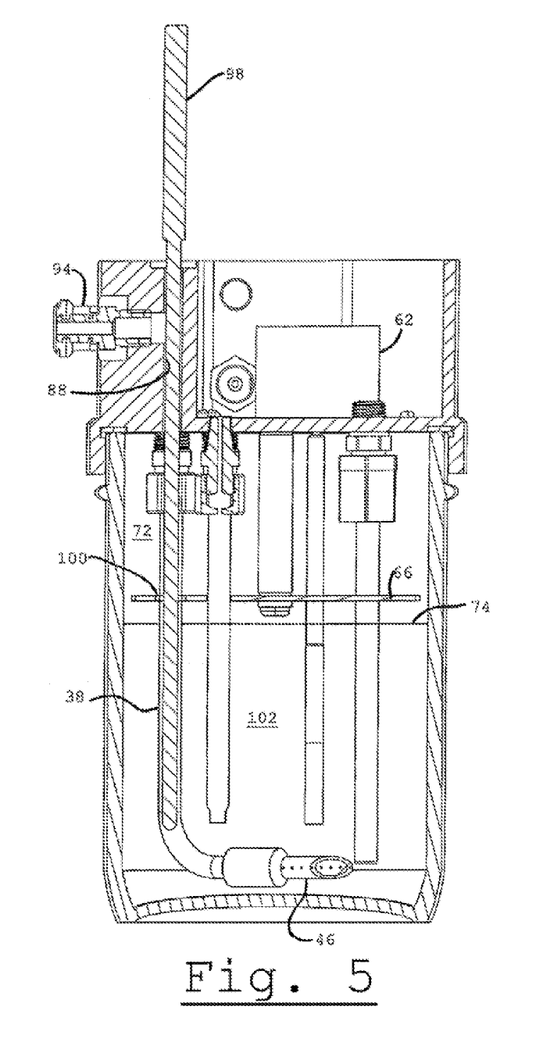
FIG. 5 is a sectional view similar to the view of FIG. 4.

Plug 90 is exposed through circular opening 96 in cover 76. When the plug 90 is removed, a temperature sensor 98 may be inserted through passage section 88, down through head space 72, through an aligned opening 100 in plate 66 and into the water/ethyl alcohol solution 102 in the bottom of jar 14 as illustrated in FIG. 5 in order to determine the temperature of the solution accurately, independently of sensors 52 and 54. Sensor 98 may be the temperature-sensing probe of an electronic thermometer.

Figure 9:
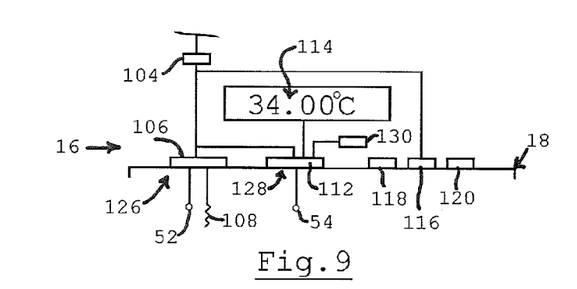
FIG. 9 is a diagram illustrating temperature control circuitry for the simulator.

FIG. 9 illustrates electrical circuitry used to monitor and control the temperature of the solution in the jar and the temperature of the lid 18 and projection 24 during operation of the simulator.

Figure 10:
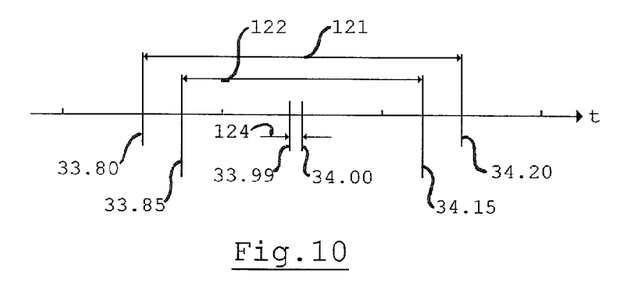
FIG. 10 is a temperature scale for the heated solution in the jar.

Temperature control circuit 126 includes a set point switch controller 106 which actuates the heater 108 in the lower end of heater rod 64 to maintain the solution temperature in a normal operating range 124 of 33.99° C. to 34.00° C. as illustrated in FIG. 10. Circuit 126 actuates heater 108 when the solution temperature falls to 33.99° C. and deactuates the heater when the temperature of the solution rises to 34.00° C. as determined by sensor 52.

Temperature monitoring circuit 128 includes a set point switch controller 112 responsive to temperature sensor 54 in solution 102. The circuit 128 also includes display 114 and alarm sounder 130. Controller 112 generates a solution temperature signal for solution temperature display 114 when the temperature for the solution is in simulator allowable operating range 122 between 33.85° C. and 34.15° C. as determined by sensor 54. The normal operating range 124 is located in the center of the allowable operating range 122, essentially equidistance between range 122 high temperature 34.15° C. and range 122 low temperature of 33.85° C.

Simulator 10 includes a lid temperature controller 116, a resistance heater 118 on the lid, and a temperature sensor 120 on lid 18. The sensor 120 sends a lid temperature signal to controller 116, which actuates heater 118 when the temperature of the lid falls below a set point temperature. The on set point temperature may be 35.8° C. so that the heater 118 heats conductive aluminum body 16 when the temperature in the lid falls below 35.8° C. The controller may have an off set point temperature of 36.2° C.

Heater 118 heats the metal body 16, including the passage projection 24. The heated projection forms a thermal mass which stores heat and heats the breath sample flowed through the inlet passage and the vapor flowed through the outlet passage. If desired, another heater also actuated by controller 116 may be mounted on the thermal mass to heat the mass directly.

Controller 116 maintains the temperature of body 16 at a temperature higher than the solution temperature in order to maintain the temperature of the vapor in the headspace at a temperature of 34°±0.5° C. The higher temperature is required because of heat loss. The operation of controller 116 to maintain the temperature of the vapor in the head space is more fully explained in U.S. Pat. No. 7,493,793, assigned to Guth Laboratories, Inc. of Harrisburg, Pa., assignee of the present application. The disclosure of U.S. Pat. No. 7,493,793 is incorporated herein by reference, in its entirety.

NHTSA standards require that the temperature of the solution be maintained within a regulatory allowable operating range 121 between 33.8° C. and 34.2° C. during operation of the simulator to calibrate a breath test analyzer. The regulatory allowable operating range has a width of 0.4° C. as shown in FIG. 10. The range extends 0.2° C. to either side of a nominal solution temperature of 34.0° C.

Temperature control circuit 126 maintains the temperature of the solution in the jar within a narrow normal operating range 124 of 0.01° C. Range 124 has a high limit of 34.00° C. and a low limit of 33.99° C. The range 124 is located in the center of the NHTSA allowable range 121 and has a temperature width 1/40th of the width of range 121.

Temperature monitoring circuit 128 monitors the temperature of the solution in the jar as determined by sensor 54. Circuit 128 is completely separate from circuit 126. When the temperature of the solution in the jar is within a simulator allowable operating range 122 the controller 112 of circuit 128 generates a temperature signal for the solution which is shown on display 114. During normal operation of the simulator, the temperature on display 114 will be within the narrow normal operating range 124, close to the nominal temperature of 34.00° C.

In the event the temperature of the solution falls below the range 122 lower limit of 33.85° C. or rises above range 122 upper limit of 34.15° C., circuit 128 automatically shuts down the simulator by deactivating temperature control circuit 126, the lid heater and the agitator motor 62. The temperature display is blanked. Alternate "Error" and "Temperature High" or "Temperature Low" signals are shown on display 114 and an alarm signal is broadcast by sounder 130 to indicate that the simulator has been shut down.

During operation of the simulator, components of the temperature control circuit 126 may drift so that the temperature at which heater 108 is actuated may move slightly from the desired low temperature of 33.99° C. and the temperature at which the heater 108 is deactuated may move slightly from the desired high temperature of 34.00° C. The effect of drift in circuit 126 is to move the on and off temperature limits for range 124 slightly. Movement of range 124 due to drift does not move range 124 outside of the simulator allowable operating range 122. See FIG. 10.

The components of temperature monitoring circuit 128 may also drift so that the solution temperature indicated on display 114 may vary slightly from the actual temperature of the solution. The operating range 124 is small relative to the simulator allowable operating range 122 so that during normal operation of the simulator, drift of components in the temperature monitoring circuit 128 does not result in display of a temperature outside of range 122.

In the event of failure of components of the temperature monitoring circuit 128, the circuit blanks the temperature display 114 and generates a shut down display and actuates alarm 130.

Prior to use of simulator 10 to calibrate a breath test analyzer, the simulator must be calibrated to assure that it accurately maintains the temperature of the solution in the jar in range 124, and to assure that the temperature display 114 accurately displays solution temperature. Calibrating of the simulator is performed by turning on the circuitry and motor 62, and heating the solution in the jar, the vapor in headspace and the top housing to operational temperatures as described.

After the simulator is at operational temperatures, plug is removed and temperature sensor 98 is inserted into passage portion 88 and down into solution 102 in the jar, as illustrated in FIG. 5. The temperature of the solution determined by sensor 98 is noted. If the temperature of the solution determined by sensor 98 is not within range 124, the set points for controller 106 are adjusted so that the temperature control circuit 126 maintains the temperature of the solution in range 124.

After the temperature control circuit 106 has been adjusted to maintain the temperature of the solution in range 124, controller 112 of the temperature monitoring circuit 128 is adjusted so that the temperature of display 114 corresponds to the solution temperature.

After calibration of the simulator 10 is completed, the sensor 98 is removed from passage portion 88 and plug 90 is reattached to close the outlet passage.

During operation of the simulator 10, display of a "Temperature High" or "Temperature Low" or "Error" signal and sounding of alarm 130 indicates that the temperature of the solution in the jar, as determined by sensor 54, is outside simulator allowable range 122 and close to the high or low limits of the regulatory allowable operating range 121 and, as a result, the simulator should not be used to calibrate a breath test analyzer. The simulator is shut down when the solution temperature is outside the simulator allowable range but still inside the regulatory allowable range. Shut down of the simulator while the solution temperature is in the regulatory allowable range assures that the simulator cannot be used to calibrate an analyzer when the solution temperature is outside the regulatory allowable operating range.

When the simulator is shut down, it must be withdrawn from use and serviced to assure that the circuit components are operating properly, following which the simulator must be recalibrated, as indicated above.

Operation of simulator 10 to calibrate a breath test analyzer will now be described.

Prior to calibrating a breath test analyzer, jar 14 is filled with an appropriate volume of water/ethyl alcohol solution up to a level slightly below plate 66 as illustrated in the drawings. The simulator vapor outlet port 94 is connected to the vapor inlet of the breath test analyzer. The air inlet port 44 of the simulator is connected to a tube for delivery of breath sample air to the simulator to generate a volume of vapor saturated with a known concentration of alcohol for delivery to the analyzer.

The simulator is then turned on to rotate agitator 60, heat the solution 102 in the jar and the vapor in the headspace and heat the lid and the passage projection thermal mass and the passages in the mass as described. Heating of the simulator and solution from an ambient temperature to a stable operational temperature may take as little as ten minutes, depending upon the ambient temperature. After heating and stabilization of the solution, the solution will be at temperature in range 124 and temperature display 114 will indicate the solution temperature.

The operator then checks to assure that the temperature display 114 indicates the solution temperature and the temperature is in range 121. The presence of a temperature display indicates that the simulator is operating properly.

Breath sample air is then blown into the simulator through port 44. The breath sample passes through warmed inlet passage 42, 40 and is bubbled up into the solution. The heated and temperature stable thermal mass in projection 24 warms the breath sample to the temperature of the solution so that the sample does not cool the solution. Flow of an unheated inlet sample into the solution would undesirably lower the temperature of the solution, requiring additional heating to maintain the solution in range 124.

The breath sample is bubbled up through the solution to form a headspace vapor saturated with alcohol vapor. The vapor is flowed through outlet passage 88, 92 to the analyzer being calibrated.

If sensor 54 determines the temperature of the solution in the jar is outside the simulator operating range 122, the temperature display is blanked and alternate "Error" and "Temperature High" or "Temperature Low" signals are displayed. The circuitry 128 for display 114 is independent of the circuitry 126 for heater 108 and is not affected by drift or possible failure of components in the circuitry 126.

Display 114 is blanked when the components of either circuit drift or fail and the solution temperature is or is sensed to be outside of range 122. The simulator 10 uses independent temperature control circuit 126 and independent temperature monitoring circuit 128 to assure automatic indication when the solution temperature moves outside of the simulator allowable operating range 122. The use of two independent circuits assures that malfunction of either circuit will alert the operator of a malfunction so that the simulator can be withdrawn from use and the problem can be corrected.

While we have illustrated and described preferred embodiments, it is understood that these are capable of modification, and we therefore do not wish to be limited to the precise details set forth, but desire to avail ourselves of such changes and alterations as fall within the purview of the following claims.

What we claim as our invention:

1. A breath test simulator for producing breath test vapor having a known concentration of ethyl alcohol at a simulator outlet port for flow from the outlet port, through an outlet tube to a breath test analyzer;

the simulator comprising a container adapted to receive a water/ethyl alcohol solution having a known concentration of ethyl alcohol; a top housing comprising a lid closing the top of the container and a one-piece thermally conductive metal body, the metal body forming at least a portion of the lid and including a thermal mass extending a distance above the lid and having an exterior surface above the lid; an inlet port on the thermal mass exterior surface; an inlet passage in the thermal mass and lid extending from the inlet port to the interior of the container; an outlet port on the thermal mass exterior surface; an outlet passage in the thermal mass and lid extending from the interior of the container to the outlet port, wherein said one-piece thermally conductive body forms the interior walls of said passages;

a first heater on said metal body for heating the lid by conduction to heat the head space in the container and for heating the thermal mass by conduction to heat the inlet and outlet passages; a first control circuit for actuating and deactuating the first heater to maintain the temperature of the head space within a first operating range; a second heater located in the interior of the container; and a second control circuit for actuating and deactuating the second heater to maintain the temperature of a water/ethyl alcohol solution in the container within a second operating range; wherein said first heater heats both inlet air flowed through the inlet passage and into the interior of the container and breath test vapor flowed through the outlet passage to the outlet port by conduction through the metal body.

2. The breath test simulator as in claim 1 wherein the thermal mass includes a side surface extending above the lid, and one of said inlet port and said outlet port is located on said side surface.

3. The breath test simulator as in claim 2 wherein both said inlet port and said outlet port are located on said side surface.

4. The breath test simulator as in claim 2 wherein the thermal mass extends partially around the circumference of the container, and the thermally conductive metal body includes a wall joined to the thermal mass and extending around the circumference of the container.

5. The breath test simulator as in claim 4 including a cover overlying the thermal mass and the wall to define an interior space above the lid, said first and said second control circuits in said space.

6. The breath test simulator as in claim 5 wherein said wall and said thermal mass extend completely around the circumference of the container, and said cover includes a portion on one side of the container; and a temperature display responsive to a control circuit on said cover portion.

7. The breath test simulator as in claim 1 wherein said one-piece thermally conductive body is made of aluminum.

8. The breath test simulator as in claim 1 wherein the first control circuit and the second control circuit are independent of each other.

9. The breath test simulator as in claim 1 wherein said thermally conductive body includes one-piece heat flow paths extending from said first heater through said thermal mass and to said inlet and outlet passages.

10. A breath test simulator for producing breath test vapor having a known concentration of ethyl alcohol for flow to a breath test analyzer, the simulator comprising a container adapted to receive a water/ethyl alcohol solution having a known concentration of ethyl alcohol; a thermally conductive metal body, the body comprising a heat radiating lid facing the interior of the container and a heat storage thermal mass extending above the lid and having a surface above the lid; an inlet port; an inlet passage extending from the inlet port to the interior of the container; an outlet port on the surface of the thermal mass; an outlet passage extending through the lid and the thermal mass from an opening on the lid to the outlet port; said lid and thermal mass forming the interior wall of the outlet passage for heat flow from the thermal mass into the passage; a first heater located in the container; a first control circuit for actuating and deactuating the first heater to maintain the temperature of a solution in the container within a first temperature range; a second heater on the conductive body; a second control circuit for actuating and deactuating the second heater to maintain the temperature of the lid within a second temperature range substantially the same as or above the first temperature range;

wherein said heat storage thermal mass stores thermal energy and heats the length of the outlet passage to heat breath test vapor flowed from the container through the outlet passage when the second heater is not actuated.

11. The breath test simulator as in claim 10 wherein said inlet passage extends through the heat storage thermal mass so that the mass heats breath test sample air flowed through the inlet passage and into the water/ethyl alcohol solution in the container.

12. The breath test simulator as in claim 11 wherein said inlet passage and said outlet passage are located side-by-side in the thermal mass, and the thermal mass is formed from a one-piece metal body.

13. The method of calibrating a breath test analyzer comprising the steps of:
   a. maintaining a water/ethyl alcohol solution in a simulator chamber at a temperature in a first operating range by actuating and deactuating a first heater in the solution;
   b. maintaining a headspace in the chamber above the solution at a temperature in a second operating range by actuating and deactuating a second heater mounted on a one-piece conductive metal top member above the simulator chamber;
   c. flowing heat from the second heater to a thermal mass forming part of the top member and extending above the chamber to heat the thermal mass;
   d. storing heat in the thermal mass when the second heater is actuated and when the second heater is deactuated;
   e. flowing breath test vapor from the head space through an outlet passage in the heated thermal mass and to an outlet port on the outside of the simulator; and
   f. flowing heat stored in the heated thermal mass into the outlet passage along the length of the passage to the outlet port to heat the breath test vapor when the second heater is actuated and when the second heater is deactuated.

14. The method of claim 13 including the step of:
   g. flowing a breath test sample through an inlet passage extending through the thermal mass and into the simulator chamber and flowing heat from the thermal mass into the breath test sample in the inlet passage to heat the breath test sample and reduce the time required to warm a solution in the chamber to the first operating range.

15. A breath test simulator for producing breath test vapor having a known concentration of ethyl alcohol at a simulator outlet port for flow from the outlet port, through an outlet tube and to a breath test analyzer; the simulator comprising a container adapted to receive a water/ethyl alcohol solution having a known concentration of ethyl alcohol; a top housing comprising a lid closing the top of the container and a thermally conductive body forming a portion of the lid and having an interior surface facing the interior of the container and an exterior surface facing out from the container; an inlet port on the top housing; an inlet passage in the top housing and extending from the inlet port to the interior of the container; an outlet port on the conductive body exterior surface; an outlet passage in the conductive body extending from the interior of the container to the outlet port, the conductive body forming the interior wall of the outlet passage extending from the interior of the container to the outlet port; a heater for heating the conductive body; and a first control circuit for actuating and deactuating the heater; wherein the heater heats the conductive body to store heat in the conductive body and stored heat from the conductive body flows through the interior wall of the outlet passage to heat breath test vapor in the outlet passage both when the heater is actuated and deactuated.

16. The breath test simulator as in claim 15 wherein the conductive body includes a side surface extending above the lid and said outlet port is located on said side surface.

17. The breath test simulator as in claim 16 wherein said inlet passage is located in said conductive body.

18. The breath test simulator as in claim 15 wherein the top housing includes an interior space and a cover over the interior space, said control circuit and heater in said space.

19. The breath test simulator as in claim 18 wherein the cover includes a portion on one side of the container, and a temperature display on said cover portion.

20. The breath test simulator as in claim 15 wherein the conductive body comprises a one-part metal piece.

21. The breath test simulator as in claim 15 wherein the conductive body comprising plural metal pieces.

* * * * *